United States Patent [19]

McKinnie et al.

[11] Patent Number: 4,778,933

[45] Date of Patent: Oct. 18, 1988

[54] PROCESS FOR MAKING DECABROMODIPHENYL OXIDE

[75] Inventors: Bonnie G. McKinnie, Magnolia, Ark.; Meng-Sheng Ao, Baton Rouge, La.

[73] Assignee: Ethyl Corporation, Richmond, Va.

[21] Appl. No.: 73,704

[22] Filed: Jul. 15, 1987

[51] Int. Cl.$^4$ .......................................... C07C 43/192
[52] U.S. Cl. ..................... 568/639; 568/631
[58] Field of Search ................. 568/639, 631

[56] References Cited

U.S. PATENT DOCUMENTS

| 3,763,248 | 10/1973 | Mitchell | 568/639 |
| 3,965,197 | 6/1976 | Stepniczka | 568/639 |
| 4,287,373 | 9/1981 | Garman et al. | 568/639 |
| 4,521,633 | 6/1985 | Pedjac | 568/639 |

FOREIGN PATENT DOCUMENTS

| 2236362 | 2/1974 | Fed. Rep. of Germany | 568/639 |
| 1411524 | 10/1975 | United Kingdom | 568/639 |

*Primary Examiner*—Werren B. Lone

*Attorney, Agent, or Firm*—John F. Sieberth; Edgar E. Spielman, Jr.

[57] ABSTRACT

The process comprises: (a) initiating a feed of molten diphenyl oxide to a substantially anhydrous mixture of methylene dibromide solvent, elemental bromine ($Br_2$) and an aluminum trihalide catalyst at a temperature between about 10° and about 30° C.; (b) heating the reaction mixture to about 50°–60° C., and while maintaining the temperature at about 50°–60° C., continuing the feed of molten diphenyl oxide until the total amount fed is equivalent to (i) about 0.064 to about 0.077 mole per mole of elemental bromine ($Br_2$) employed in the reaction, and (ii) about 0.2 to about 10 parts by weight per part by weight of methylene dibromide employed in the reaction; (c) steam distilling the methylene dibromide solvent and the residual bromine from the reaction mixture; (d) recovering decabromodiphenyl oxide from the distilland; and (e) drying the methylene dibromide and bromine distillate to render them suitable for reuse in the process.

5 Claims, No Drawings

PROCESS FOR MAKING DECABROMODIPHENYL OXIDE

FIELD

This invention relates to an efficacious process for the manufacture of decabromodiphenyl oxide, a commercial flame retardant.

BACKGROUND

U.S. Pat. No. 3,763,248 discloses the polybromination of aromatic compounds including diphenyl ether (diphenyl oxide) with bromine using certain metal halide halogenation catalysts such as $AlCl_3$ and $AlBr_3$ and solvent quantities of methylene bromide. The amount of bromine used is from 4 to about 12 moles of bromine per mole of aromatic compound to be brominated. The amount of methylene bromide is from about 8 to about 20 moles and preferably from 10 to about 15 moles per mole of aromatic compound.

British No. 1,411,524 describes bromination of aromatic compounds including diphenyl oxide by gradual addition of one reactant to the other while maintaining the quantity of bromine throughout the reaction at a minimum excess of 20 percent with respect to the quantity stoichiometrically necessary for the reaction. The process is conducted in the absence of a solvent. Decabromdiphenyl ether was prepared by gradually adding 0.3 moles of molten diphenyl oxide to 5 moles of bromine and 2.5 g of anhydrous aluminum chloride.

To the same general effect is U.S. Pat. No. 3,965,197 which describes production of decabromodiphenyl oxide by adding molten diphenyl oxide (diphenyl ether) to a large stoichiometric excess of liquid bromine containing a halogenation catalyst such as aluminum trihalide (U.S. Pat. No. 3,965,197). Although it is not a solvent, the large excess of bromine acts as a liquid medium in which the product is suspended and from which it can be recovered.

Because of its expense, the excess bromine remaining at the conclusion of the reaction must be recovered for reuse. In order to have a manageable reaction mixture and a satisfactory product yield, U.S. Pat. No. 3,965,197 specifies that the large excess of liquid bromine that is used is at least 100 percent of the stoichiometric amount of bromine required for the complete bromination. Thus for every mole of diphenyl oxide used in the process, the reaction system must contain at least 20 moles of elemental bromine. In U.S. Pat. No. 4,287,373, a similar process is described in which the sole liquid reaction medium is composed of at least a 75 percent excess and not more than a 400 percent excess of the stoichiometric amount. In other words, the liquid reaction medium has 17.5 up to 50 moles of bromine per mole of diphenyl oxide.

In other processes, it has been found possible to effectively produce decabromodiphenyl oxide using a 60-70 percent excess of bromine.

Despite the need to use such large excesses of liquid bromine, U.S. Pat. No. 4,287,373 points out that the use of solvents along with smaller excesses of bromine results in serious difficulties. In the words of the patentee:

"Prior art perbromination processes in general have involved use of an up to about 20% excess of bromine in the presence of various kinds of reaction media and solvents such as ethylene dibromide, carbon tetrachloride, chloroform, methylene bromide, acetylene tetrachloride, and the like depending on the particular aromatic compound to be brominated. Perbromination of aromatic compounds has also been carried out in reaction media such as oleum, concentrated sulfuric acid, fuming sulfuric acid, liquid sulfur dioxide, and the like.

Each of these process approaches has serious disadvantages for perbromination, especially for commercial operations. The use of halogenated organic solvents has disadvantages which include low productivities, undersirably slow reaction rates, and the necessity for recovery of the solvents for recycle. In some cases this technique results in the introduction of small but significant amounts of chlorine into the final product, thus limiting product quality. In addition a number of non-condensed aromatic compounds do not undergo perbromination satisfactorily under conditions which can readily be employed using halogenated organic solvents."

THE INVENTION

A process has now been discovered in which the need for such large excesses of bromine has been eliminated. In addition, a process has now been discovered which permits use of a solvent which does not pose the serious difficulties quoted above. Moreover, the process of this invention possesses certain advantages in that the solvent employed aids in the recovery of elemental bromine and, in that only traces of an innocuous impurity were detected in the solvent which would not impair its usefulness in recycle.

The process of this invention comprises in combination, the following steps:
 (a) initiating a feed of molten diphenyl oxide to a substantially anhydrous mixture of methylene dibromide solvent, elemental bromine ($Br_2$) and an aluminum trihalide catalyst at a temperature between about 10° and about 30° C.;
 (b) heating the reaction mixture to about 50°–60° C. and while maintaining the temperature at about 50°–60° C., continuing the feed of molten diphenyl oxide until the total amount fed is equivalent to (i) about 0.064 to about 0.077 mole per mole of elemental bromine ($Br_2$) employed in the reaction, and (ii) about 0.2 to about 10 parts by weight per part by weight of methylene dibromide employed in the reaction;
 (c) steam distilling the methylene dibromide solvent and the residual bromine from the reaction mixture;
 (d) recovering decabromodiphenyl oxide from the distilland; and
 (e) drying the methylene dibromide and bromine distillate to render them suitable for reuse in the process.

In terms of stoichiometry, the above molar ratio of 0.077:1 translates to a 30 percent excess of bromine over the stoichiometric amount whereas the above molar ratio of 0.064 is equivalent to an excess of about 55 percent above theoretical. The most preferred range (mole diphenyl oxide: mole $Br_2$) for the process is from about 0.071:1 (40 percent excess) to about 0.077:1 (30 percent excess).

The amount of methylene dibromide solvent falls in the range of about 0.1 to about 5 parts by weight per each part by weight of diphenyl oxide fed in steps (a)

and (b) above. A feature of the invention is the fact that the methylene dibromide is readily stripped from the reaction mixture along with the residual bromine by means of the steam distillation. Furthermore, since the methylene dibromide is higher boiling than bromine, it aids in removal of the bromine from the reaction product by serving in part as a chaser. Preferably, the reaction system will contain from about 0.5 to about 2.0 parts weight of methylene dibromide per each part by weight of diphenyl oxide fed in (a) and (b) above as this provides the foregoing advantages while making most efficient use of reactor space. In other words, the amount of diphenyl oxide fed to the system is preferably about 0.5 to about 2 parts by weight per part by weight of methylene dibromide employed in the reaction.

In another preferred embodiment of this invention, the reaction mixture is maintained at reflux temperature during at least a substantial portion of the time molten diphenyl oxide is fed in (b).

The catalyst used in the process is preferably $AlCl_3$ and/or $AlBr_3$ although use may be made of $FeCl_3$ and/or $FeBr_3$ alone or in combination with the aluminum trihalide(s). Catalytic quantities are, of course, used—typically from about 0.1 to about 20, and preferably from about 1 to about 10, weight percent based on the weight of diphenyl oxide used in the process.

Although the diphenyl oxide may be added to the reaction mixture as a solid, it is preferably added molten since its melting point is low (about 27° C.). To prevent freeze up in the feed conduit, it is typically fed at temperatures of about 28° to 35° C. although even higher melt temperatures can be employed if desired.

The addition of the diphenyl oxide to the reaction mixture occurs over a period of time. Feed time depends on scale and ability to control temperature and handle hydrogen bromide evolution. On a laboratory scale the addition typically requires about 0.5 to 2 hours. On a commercial scale, feed to the reaction could involve about 2 to 10 hours or longer. Four hours is typical. After completion of the feed, the reaction mixture can, if desired, be held for a period to assure that perbromination has been achieved to the desired extent. A period of up to one hour at or near reflux is beneficial for this purpose.

The following example further illustrates the practice of this invention and results achievable therefrom.

EXAMPLE

In a 500 mL Morton flask equipped with a polytetrafluoroethylene sealed mechanical stirrer, 5° C. Friedrich condenser, thermometer, addition funnel equipped with a dip-tube, and heating mantle were placed 125 mL bromine (2.44 g-atom), 30 mL methylene dibromide, and 1.82 g of $AlCl_3$. This mixture was heated to 50° C. and 30 mL of diphenyl oxide was added over a 2.5 hour period while holding the temperature at 60°–70° C. Water was added to the reaction mixture and the bromine and methylene dibromide were distilled out. The decabromodiphenyl oxide was isolated in 98.8 percent purity in high yield (essentially quantitative) by adding NaOH to destroy residual bromine followed by filtration, washing the filter cake with water, and drying. It melted at 307°–314° C. The bromine-methylene dibromide distillate was added slowly to 70.4g (95 percent recovery). VPC analysis on a SP-1000 column showed the only impurity in the methylene dibromide was 0.2 percent bromoform ($CHBr_3$).

As reported in U.S. Pat. No. 3,075,944, the disclosure of which is incorporated herein by reference, decabromodiphenyl oxide is a useful flame retardant additive for various polyolefins, including polystyrene. It is also useful as a flame retardant for various other polymers such as ABS, polyesters, rubbers, and epoxy resins. It is typically used in combination with antimony trioxide.

This invention is susceptible to considerable variation within the spirit and scope of the appended claims.

What is claimed is:

1. A process for producing decabromodiphenyl oxide which comprises:
   (a) initiating a feed of molten diphenyl oxide to a substantially anhydrous mixture of methylene dibromide solvent, elemental bromine ($Br_2$) and an aluminum trihalide catalyst at a temperature between about 10° and about 30° C.;
   (b) heating the reaction mixture to about 50°–60° C. and while maintaining the temperature at about 50°–60° C., continuing the feed of molten diphenyl oxide until the total amount fed is equivalent to (i) about 0.064 to about 0.077 mole per mole of elemental bromine ($Br_2$) employed in the reaction, and (ii) about 0.2 to about 10 parts by weight per part by weight of methylene dibromide employed in the reaction;
   (c) steam distilling the methylene dibromide solvent and the residual bromine from the reaction mixture;
   (d) recovering decabromodiphenyl oxide from the distilland; and
   (e) drying the methylene dibromide and bromine distillate to render them suitable for reuse in the process.

2. The process of claim 1 in which the amount of the methylene dibromide solvent employed in the reaction is equivalent to about 0.5 to about 2.0 parts by weight per each part by weight of diphenyl oxide fed in (a) and (b).

3. The process of claim 1 in which the reaction mixture is maintained at reflux temperature during at least a substantial portion of the time molten diphenyl oxide is fed in (b).

4. The process of claim 1 in which the total amount of molten diphenyl oxide fed is equivalent to about 0.071 to about 0.077 mole per mole of elemental bromine ($Br_2$) employed in the reaction.

5. The process of claim 1 in which the amount of the methylene dibromide solvent employed in the reaction is equivalent to about 0.5 to about 2.0 parts by weight per each part by weight of diphenyl oxide fed in (a) and (b), in which the reaction mixture is maintained at reflux temperature during at least a substantial portion of the time molten diphenyl oxide is fed in (b), and in which the total amount of molten diphenyl oxide fed is equivalent to about 0.071 to about 0.077 mole per mole of elemental bromine ($Br_2$) employed in the reaction.

* * * * *

UNITED STATES PATENT AND TRADEMARK OFFICE
CERTIFICATE OF CORRECTION

PATENT NO. : 4,778,933

DATED : October 18, 1988

INVENTOR(S) : Bonnie G. McKinnie, et al

It is certified that error appears in the above-identified patent and that said Letters Patent is hereby corrected as shown below:

Cover page, column 1, under References Cited, U.S. Patent Documents, the following were omitted:

```
3,285,965   11/1965   Jenker
3,833,674    9/1974   Brackenridge
3,959,387    3/1976   Brackenridge
3,965,197    6/1976   Stepniczka
4,287,373    9/1981   Garman, et al.
```

Cover page, column 1, under References Cited, Foreign Patent Documents, the following were omitted:

```
 981833    1/1965   United Kingdom
 991067    5/1965   United Kingdom
1472383    5/1977   United Kingdom
 708209    5/1965   Canada
53 116332 10/1978   Japan
52  39639  3/1977   Japan
53 116334 10/1978   Japan
2950877    6/1981   West Germany
```

UNITED STATES PATENT AND TRADEMARK OFFICE
CERTIFICATE OF CORRECTION

PATENT NO. : 4,778,933

DATED : October 18, 1988

INVENTOR(S) : Bonnie G. McKinnie, et al

It is certified that error appears in the above-identified patent and that said Letters Patent is hereby corrected as shown below:

Column 4, lines 2 and 3, read "to 70.4g (95 percent recovery)." and should read -- to cold dilute sodium sulfite and the methylene dibromide separated giving 70.4g (95 percent recovery). --.

Signed and Sealed this

Second Day of May, 1989

Attest:

DONALD J. QUIGG

Attesting Officer

Commissioner of Patents and Trademarks